United States Patent [19]
Feld et al.

[11] Patent Number: 5,260,026
[45] Date of Patent: Nov. 9, 1993

[54] APPARATUS FOR PREPARING PHOSPHORUS TRICHLORIDE

[75] Inventors: Macaulay S. Feld, Ellisville; David O. Fisher, Chesterfield; John F. Freeman, Webster Groves; Gregory J. Gervasio, Glencoe; Mark A. Hochwalt, Chesterfield; Leonard F. Laskowski, Clayton; Evan E. Thomsen, Florissant, all of Mo.

[73] Assignee: Monsanto Company, St. Louis, Mo.

[21] Appl. No.: 807,353

[22] Filed: Dec. 16, 1991

Related U.S. Application Data

[63] Continuation-in-part of Ser. No. 726,490, Jul. 8, 1991, abandoned.

[51] Int. Cl.$^5$ ............................................. G01N 21/00
[52] U.S. Cl. ..................... 422/62; 422/82.06; 422/203; 436/55; 356/301; 364/498; 364/500
[58] Field of Search ............... 422/62, 82.06, 203; 436/55; 356/301; 364/498, 500

[56] References Cited

U.S. PATENT DOCUMENTS

| | | | |
|---|---|---|---|
| 4,263,010 | 4/1981 | Randolph | 23/230 A |
| 4,802,761 | 2/1989 | Bowen et al. | 356/301 |
| 4,816,226 | 3/1989 | Jordan et al. | 422/81 |
| 4,892,383 | 1/1990 | Klainer et al. | 350/96.29 |
| 4,929,561 | 5/1990 | Hirschfeld | 436/116 |
| 5,102,625 | 4/1992 | Milo | 422/82.07 |
| 5,114,864 | 5/1992 | Walt | 436/528 |

OTHER PUBLICATIONS

Schumann, Rudolph; Rapid Method for Determining Elemental Phosophorus Trichloride; Chem. Tech. (Leipzig) vol. 24, No. 6, p. 363 (1972).

Kirievskaya, et al; Gas-Chromatographic Determination of White Phosphorus and of Certain Phosphorus Chloride; Zhurnal Prickladnoi Khimii, vol. 45, No. 9, pp. 2074–2076 (1972).

Ganter et al; Applications of Lasa Raman Spectrometry in Process Central Using Optical Fibers; Fresenius J. Anal Chem. vol. 338 pp. 2–8 (1990).

Keeler, R. A. et al; Analysis of Mixtures of White Phosphorus, Phosphorus Oxychloride and Phosphorus Trichloride; Anal Chem. vol. 26, No. 5, pp. 933–934 (1954).

*Primary Examiner*—James C. Housel
*Assistant Examiner*—N. Bhat
*Attorney, Agent, or Firm*—Richard H. Shear; Raymond C. Loyer; James C. Bolding

[57] ABSTRACT

There is disclosed an improved process for the preparation of phosphorus trichloride wherein elemental phosphorus is caused to react with chlorine. The improvement comprises continuous, high speed analysis of the contents of the reactor whereby the reaction is controlled to produce less phosphorus pentachloride and other by-products. The analysis is performed by a laser Raman spectrometer associated with an optrode having a remotely located probe head and a circulating sampling system to continuously provide fresh sample to the probe head continuously. Also disclosed is apparatus for the automatic control of the reaction by control of the reactant feed to the reactor in response to the on-line, continuous analysis of the reactor contents.

2 Claims, 3 Drawing Sheets

APPARATUS FOR PREPARING PHOSPHORUS TRICHLORIDE

This application is a continuation-in-part of Ser. No. 07/726,490, filed Jul. 8, 1991, now abandoned.

This invention relates to the production of phosphorus trichloride and more particularly to a process for large scale commercial production of phosphorus trichloride by the reaction of phosphorus and chlorine.

BACKGROUND OF THE INVENTION

Phosphorus trichloride is usually prepared by the direct reaction of phosphorus and chlorine in a reactor containing phosphorus trichloride. The phosphorus trichloride produced is generally removed from the reactor by distillation through utilization of the heat of reaction. The reaction takes place in phosphorus trichloride to which elemental phosphorus is added. The phosphorus dissolves into the phosphorus trichloride. Chlorine is sparged into the phosphorus trichloride to react with dissolved phosphorus. Sparging aids in dissolving the phosphorus into the phosphorus trichloride.

There are several possible reactions which can take place in the reactor which are described by the following reactions:

$$P_4 + 6Cl_2 \rightarrow 4\, PCl_3$$

$$Cl_2 + PCl_3 \rightarrow PCl_5$$

$$P_4 + 6PCl_5 \rightarrow 10\, PCl_3$$

From the above illustrated reactions, it is clear that the undesired production of phosphorus pentachloride may occur. To reduce the amount of production of this undesired product, the reaction is usually controlled by the amount of chlorine introduced into the reactor allowing for an excess of phosphorus with respect to chlorine to be present in the phosphorus trichloride.

Control of the reaction is important because phosphorus trichloride is a hazardous chemical which can severely burn skin, eyes, and mucous membranes. Vapors from minor inhalation can cause severe respiratory ailments depending upon the degree of exposure. Also, phosphorus trichloride is highly toxic and it reacts violently with water generating dangerous acids and phosphines. The heat of the reaction for the formation of phosphorus pentachloride from phosphorus trichloride and chlorine is less that the formation of phosphorus trichloride from phosphorus and chlorine. This drop in heat generation can be used to detect deficiency of phosphorus in the reactor but this mechanism is indirect. In the usual case, the reaction conditions are controlled by the rate of chlorine addition into the reactor. In general, such control is effective to prevent formation of undesirable amounts of phosphorus pentachloride. The amount of excess phosphorus in the phosphorus trichloride is maintained at a relatively high level to minimize the formation of phosphorus pentachloride and thus provide for safe and efficient operation of the process. Safety considerations are a major factor when dealing with the chemicals involved.

The problem of controlling the reaction of phosphorus and chlorine has produced various analytical methods or schemes based upon the periodic determination of elemental phosphorus in the reaction zone of the reactor. One method of determination of phosphorus is disclosed in *Chem. Tech (Leipzig)* Vol. 24, No. 6, p. 363 (1972) by Rudolph Schumann. In this method a measured sample of the phosphorus trichloride solution is withdrawn from the reactor and poured into a Dewar flask containing bromine dissolved in carbon tetrachloride. The temperature of the solution before addition of the sample is noted, and after thorough mixing, the temperature is again noted. The temperature difference is a rough measure of the phosphorus concentration as determined by comparison with a calibration curve.

Another method of analysis for phosphorus and phosphorus chlorides is gas-chromatography. Such a method is reported by M. M. Kirievskaya et al. in a publication entitled "*Gas-chromatographic Determination of White Phosphorus and of Certain Phosphorus Chlorides*" appearing in *Zhurnal Prikladnoi Khimii*, Vol. 45, No. 9, pp.2074–2076, (1972). A chromatograph was employed to determine white phosphorus and various phosphorus chlorides with a 5000×3 mm column packed with Celite 545 and SKT-FT-100× methylfluoropropylsilicone rubber. The column temperature was 150° C. and a thermoconductivity detector was used. The method was based upon mixtures of reagent grade materials mixed together in the laboratory.

The above examples of analyses require the transport of samples to the analytical apparatus and considerable delay in obtaining results. There is needed a rapid, safe and yet accurate method for controlling large scale commercial processes for the production of phosphorus trichloride.

It is therefore important that the reactor in which phosphorus trichloride is produced is very secure and is operated with control so as to assure both maximum safety as well as efficiency.

The sampling of the reaction mixture in which phosphorus trichloride is produced is a particularly difficult task when desiring to provide a representative sample to the analytical system for monitoring the reaction on a continuous basis. As noted above the reactor contains materials which must be handled with great care and contained within a closed vessel. One way to prevent leaks and spills from the reactor is to withdraw the sample from the top of the reactor. The reactor contains a boiling liquid making it difficult to withdraw a sample from the top without flashing of the liquid. Flashing occurs due to reduced pressure resulting in vapor being admitted into the sample system rather than a representative sample of the liquid reaction mixture.

BRIEF DESCRIPTION OF THE INVENTION

In accordance with the present invention there is provided an improved continuous commercial scale process for the production of phosphorus trichloride wherein phosphorus is caused to react with chlorine in a reaction zone within a closed reactor wherein the improvement comprises continuously analyzing the contents of the reaction zone for phosphorus and phosphorus pentachloride by means of a laser Raman spectrophotometer in optical communication with the reactor contents by means of an optrode and continuously adjusting the operating conditions of the reactor in response to said analysis so as to provide an excess, by weight, of phosphorus in the reaction zone.

Also in accordance with this invention the optrode is remote from the reactor and is continuously supplied with a fresh sample of the contents of the reaction zone through a sampling system comprising a pump in association with a circulatory sampling pipe wherein a continuous flow of sample material from the reaction zone is continuously circulated from the reactor to the optrode and then returned to the reactor.

A problem peculiar to laser Raman spectrometry in this application is the thermal decomposition of products on the window through which the laser light is directed toward sample material. Localized heating of the sample material at the window surface occurs if the sample material is not removed from the exposed area. Therefore, in another aspect of the process of this invention, there is provided a circulatory sampling pipe containing an eductor to continuously introduce a stream of fresh reactor contents into the sampling pipe from the reaction zone.

DETAILED DESCRIPTION OF THE INVENTION

Figure 1:
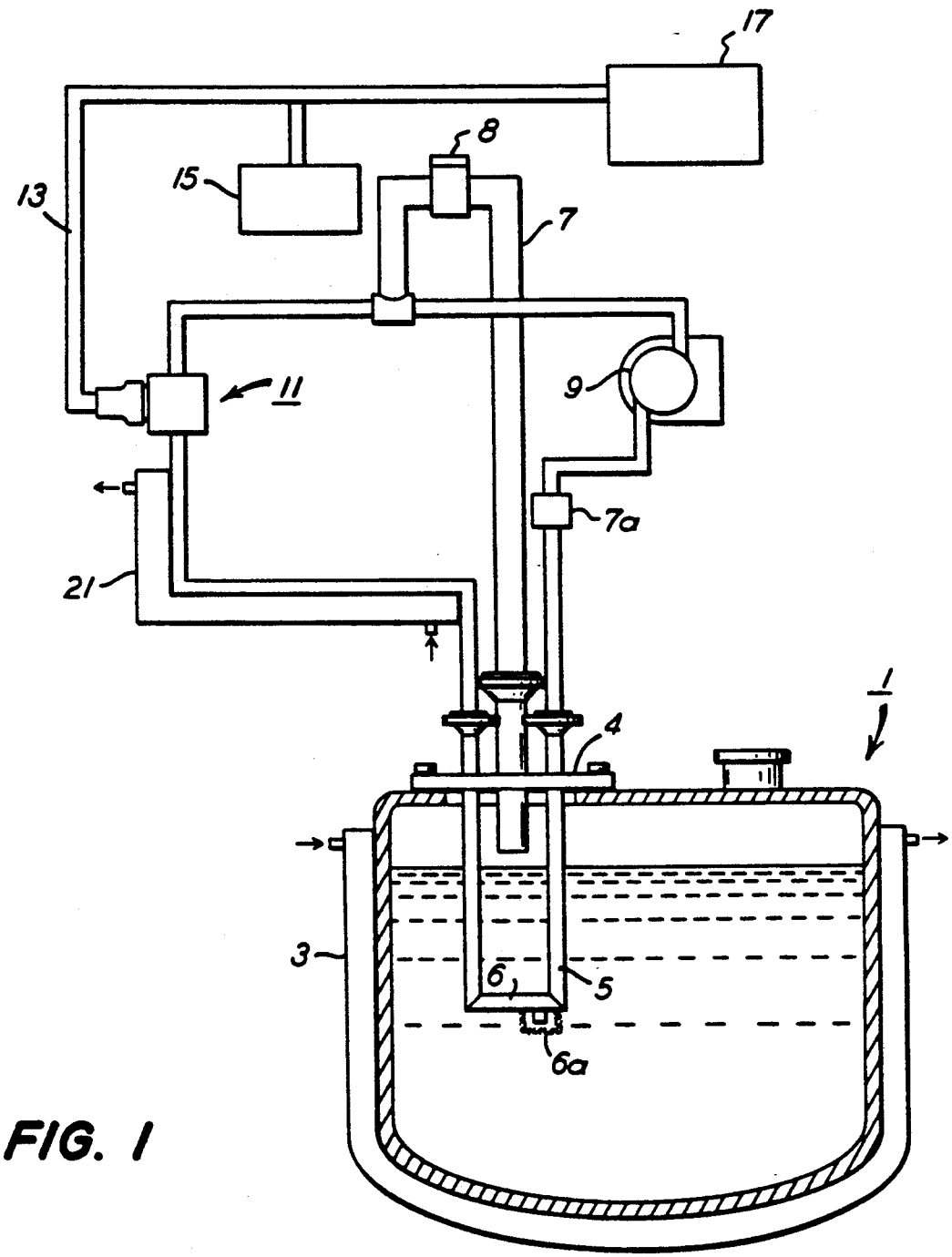
FIG. 1 is a detailed schematic diagram of an apparatus in which the process of this invention may be conducted.

In accordance with this invention there is provided a process for preparing phosphorus trichloride wherein the reaction is controlled, preferably by an automatic, electronic controlled system to provide maximum efficiency yet safe operation. The application of laser Raman spectroscopy in process control is known in the nuclear industry where hazardous materials are routinely employed yet accurate, constant control is required to attain maximum safety. A description of such utility appears in *Fresenius J. Anal. Chem.* (1990) 338 pp. 2-8, Vol. 338 by Erwin Gantner and Dieter Steinert. Possible applications in nuclear materials processing was of immediate attention to the authors, while other uses for remote control of processes by Raman spectroscopy were alluded to, such as chemical processing of galvanic waste waters. To achieve remote location of the spectrometer, optical fibers were suggested to convey information from distances of over 50 meters is proposed. A device, termed an optrode, consisting of a bundle optical fibers in combination with a laser device, was employed to sample the Raman scattered light. A more particular description of an optrode appears below.

Therefore, in one aspect of this invention there is provided a process for preparing phosphorus trichloride wherein the control of the process is obtained by a remotely placed laser Raman spectrometer as well as a remotely placed optrode which is provided with a continuous supply of fresh sample material from the reaction zone of the reactor. A circulating system for supplying materials to the optrode has been devised to enable continuous and accurate analysis of the reaction zone in which phosphorus trichloride is produced and, in turn, employ the results of such analysis to control the reaction by continuous, automatic adjustment of the reaction conditions, particularly the flow rate of chlorine to the reactor. In addition to, or alternatively, other reaction conditions may be controlled in response to the analytical results obtained by the laser Raman spectrometer. Other conditions include the amount of phosphorus trichloride allowed to remain in the reactor, the amount of elemental phosphorus added to the reactor, reactor temperature and reactor pressure. Any one or combination of the above variables can be controlled in response to the on-line analysis of the reaction zone.

Also, as a consequence of such continuous and accurate control of the reaction, the amount of excess phosphorus in the reaction zone may be maintained at a lower level than was previously believed possible. Previously, a minimum level of phosphorus was maintained in the liquid phosphorus trichloride layer of the reactor. Said amount of phosphorus was maintained so as to minimize the amount of phosphorus pentachloride by-product formed while simultaneously providing sufficient reactant for a reasonable production rate. It has now been discovered that the amount of phosphorus in the phosphorus trichloride layer may be reduced safely to at least half or less than the amount previously believed necessary while actually increasing the production rate of desired phosphorus trichloride. Thus, in accordance with this invention phosphorus trichloride is produced in greater quantities in the same reactor.

In operation, the reactor occasionally requires cleaning out because residue collects in the reactor usually introduced with the elemental phosphorus. This process involves exhaustive chlorination of all elemental phosphorus in the reactor while desirably avoiding the production of high levels of phosphorus pentachloride. Previously, the determination of the amount of remaining phosphorus was cumbersome, time consuming and therefore only roughly calculated. This resulted in either under chlorination leaving residual pyrophoric elemental phosphorus in the reactor or over chlorination resulting in the excess levels of phosphorus pentachloride. The process and apparatus of this invention has rendered the system greatly more efficient in the procedure to shut down the reaction. By means of rapid analysis and automatic control of the reactor conditions, the amount of chlorine to be added at shut down is closely regulated in accordance with the amount of residual phosphorus. The proper amount of chlorination is provided and waste products minimized.

DETAILED DESCRIPTION OF THE DRAWINGS

In FIG. 1 there is shown a schematic diagram of the apparatus of this invention. Not shown is an automatic control system in association with the remotely located laser Raman spectrometer. Such systems are well known in the art and are commercially available. One such system is sold under the trade name Provox by Fisher Control International, Inc., Austin, Tex. Typically, an automatic control system controls the amount of chlorine admitted to the reactor in response to the amount of phosphorus dissolved in the phosphorus trichloride. Other reactor conditions may also be controlled by such an automatic system such as reactor temperature, elemental phosphorus concentration, reactor pressure and phosphorus trichloride level. Such controls are operated in conjunction with an automatic system as is known in the art.

Referring again to FIG. 1, there is shown reactor 1 having a jacket 3 for temperature control. Built into the reactor is a circulatory sampling device which comprises a circulatory pipe 5 with an eductor 6 and a line, 7 to return a portion of analyzed sample from the window 11 to the reactor, all of which will be more fully described below. Strainer 7A is shown in line 5 to remove particulate material in the effort to maintain an open orifice in eductor 6. The circulatory pipe 5 of the sampling system is shown in FIG. 1 as running from Pump 9 through eductor 6 which causes, by means of the motive force of the fluid in Pipe 5, sample material to be picked up and delivered to window 11 at the end of optrode 13. Optrode 13, comprises a bundle of optical fibers around a centrally located optical fiber carrying laser generated light. In operation, optrode 13 carries laser generated light from laser 15 to the window 11 and the surrounding optical fibers conduct scattered light from the sample in pipe 5 to Raman spectrometer 17. The circulatory pipe 5 is joined to a sample return line 7 whereby a portion of the analyzed sample is removed from sampling system allowing fresh sample to be introduced at eductor 6. A flow meter 8 is shown in return line 7 to indicate the flow in line 7 which, in turn, indicates the amount of fresh sample entering the circulatory pipe 5 at eductor 6. The control of the amount of sample material allowed to flow through return line 7 is determined by the flow rate in circulatory pipe 5 and the orifice in eductor 6. Also shown in FIG. 1 is a protective screen 6a around the entrance of eductor 6 to prevent large particles from entering the eductor. The above described sample system provides a continuous flow of sample material to window 11 for analysis and consequential control of the reactor conditions.

Figure 2:
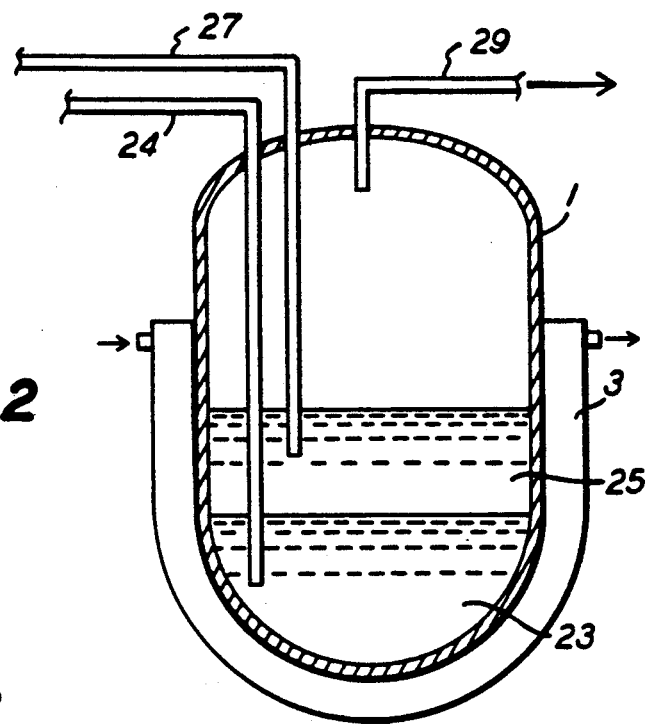
FIG. 2 is a schematic diagram of a reactor in which the process of this invention may be conducted.

Referring now to FIG. 2, there is shown a typical reactor in more detail with respect to the delivery of raw materials and recovery of product. While the invention is described with respect to the system shown in FIG. 2, it is understood that the process and apparatus of this invention may be employed in various systems for the production of phosphorus trichloride including the operation of a homogenous liquid phase reaction of chlorine with elemental phosphorus dissolved in phosphorus trichloride. In FIG. 2 there is shown reactor 1 containing a layer of liquid phosphorus 23 maintained by phosphorus feed tube 24 through which liquid phosphorus is fed to the reactor so as to maintain an adequate heel. Above layer 23 there is shown another layer 25, comprising liquid phosphorus trichloride. The content of layer 25 is maintained by constant, controlled feeding of chlorine through chlorine feed tube 27. Chlorine is sparged into the liquid layer 25 thereby creating sufficient agitation of the liquid to aid in the dissolution of phosphorus from layer 23. The reaction of phosphorus and chlorine takes place in liquid layer 25 producing the desired phosphorus trichloride which is removed in vapor form from the reactor through exit tube 29. Not shown in FIG. 2 is circulatory pipe 5 and control mechanisms for the automatic control of the flow of reactants phosphorus and chlorine as well as reflux condensers and associated equipment for the recovery of product as is well known in the art.

Figure 3:
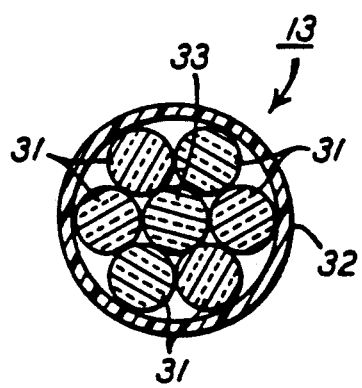
FIG. 3 is a cross section of the optrode employed in conjunction with a laser Raman spectrometer whereby information with respect to the contents of the reactor is relayed to the spectrometer.

A cross sectional view of optrode 13 is shown in FIG. 3. Surrounded by light conducting fibers 31 is a light conducting fiber 33 which carries the laser emission. In operation, the laser emission is caused to illuminate the sample liquid phosphorus trichloride brought from the reactor to the probe head of the optrode by the circulatory pipe 5. The scattered light from the illuminated sample is carried to spectrometer through light conducting fibers 31. The bundle of fibers is held together and protected by a protective sheath 32.

Rapid and continuous analysis of the contents of the reaction zone of the reactor (the liquid phosphorus trichloride layer) is thus made possible by the remotely located Raman spectrometer. The sampling system is securely fastened to the reactor providing a secure means to continuously transport material from the reactor for analysis. Analysis of the very corrosive and hazardous contents of the reaction zone of a phosphorus trichloride reactor is accomplished through window 11 because the window is transparent to the light frequencies encountered in the Raman spectrometer employed herein. Typical materials employed in window 11 are quartz, sapphire and Pyrex ® brand glass. Accurate and rapid analysis is provided without exposing the material outside of the reaction system. However, it has been found to be essential to maintain fluid motion at the face of window 11 when the laser is in operation to prevent localized thermal overheating, thermal decomposition and deposition of material (typically impurities in the sample) at the face of the window. Such thermal decomposition produces deposits on the window resulting in impaired light transmission into and out of the sample. To avoid deposits caused by thermally degraded sample, an interlock system is provided between the circulatory sample system and laser 15 whereby the laser light is blocked in the event of severely reduced or complete interruption of fluid flow in the circulatory system.

Figure 4:
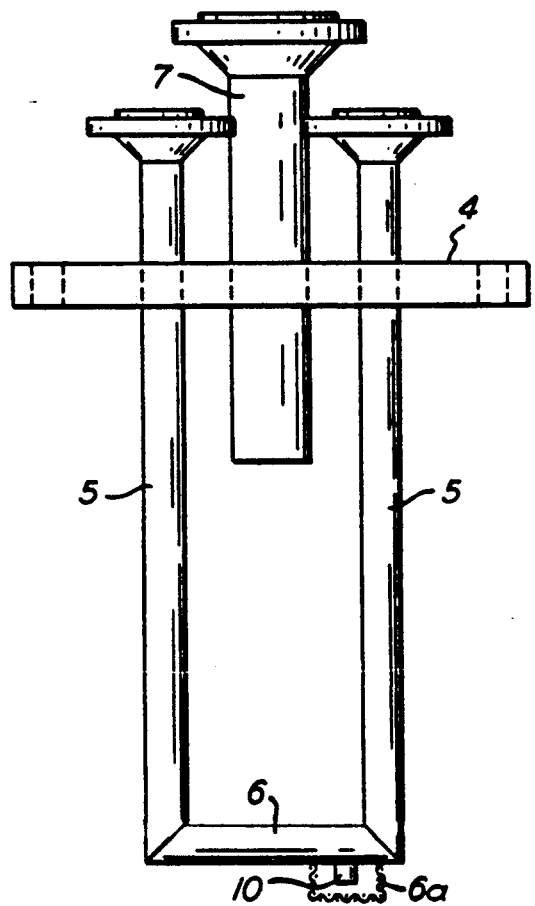
FIG. 4 is a schematic diagram of the portion of the sampling system within the reactor whereby a continuous flow of fresh sample material is circulated to the optrode.

In FIG. 4 there is shown a more detailed view of the portion of sampling system which extends into the reactor. In FIG. 4 there is shown eductor 6 at the lower end of circulatory pipe 5. Eductor 6 is submerged in layer 25 of FIG. 2. The flow of liquid across the eductor 6 in pipe 5 causes constant introduction of fresh liquid from layer 25 into eductor suction inlet 10. An excess portion of the liquid returning from the probe head of optrode 15 returns to the reactor through pipe 7. Circulatory pipe 5 is held in position and supported by flange 4.

Figure 5A:
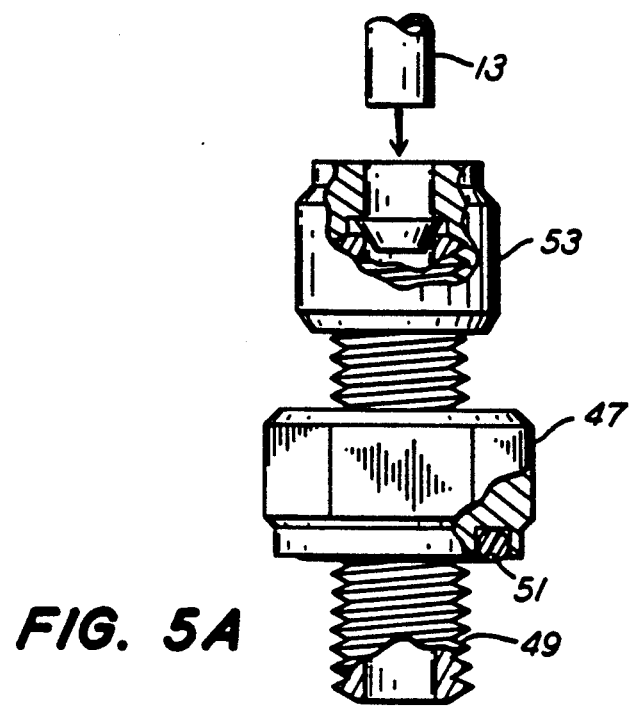
FIGS. 5 and 5a are enlarged and partially crossectional views of the window access provided in a circulatory sampling system.
Figure 5:
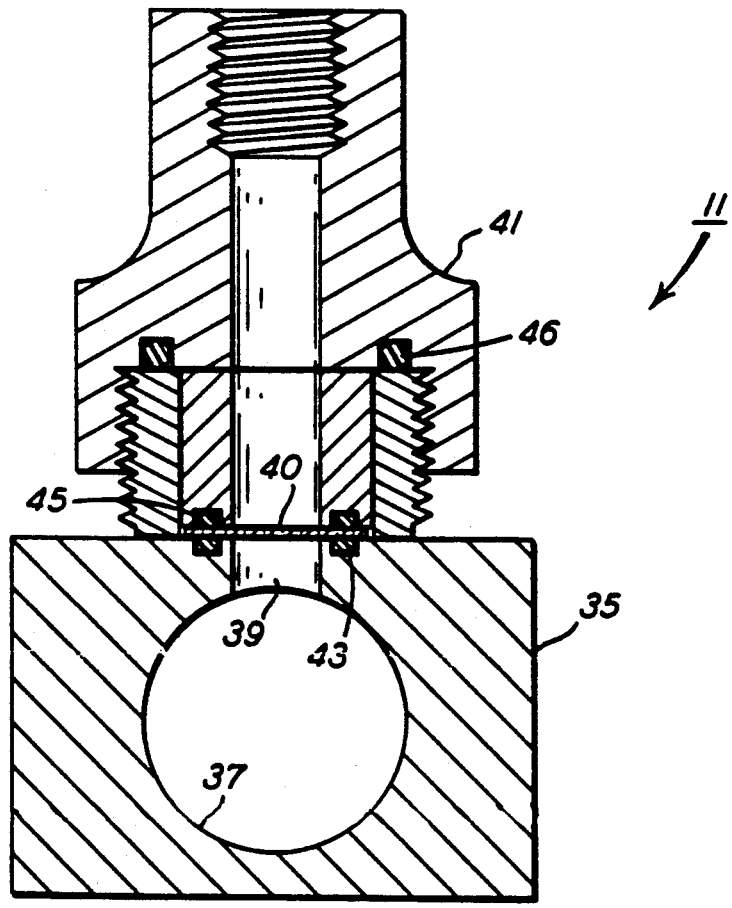

A more detailed view of window 11 is shown in FIGS. 5 and 5a. Because the components being analyzed are highly reactive and corrosive, access to the material for purposes of on-line analysis must be provided with many precautions. To provide access there was devised window block 35 having a through aperture 37 and optrode aperture 39. Block 35 is installed into circulatory pipe 5. In optrode aperture 39 is located a transparent window 40. A threaded fitting is provided to received threaded flange 41 which provides compression to seals 43 and 45 thereby sealing the transparent window 40. Seals 43 and 45 are shown in FIG. 5 as o-rings. Threaded flange 41 is itself fitted with a seal 46 which can also be an o-ring.

In FIG. 5a there is shown threaded sleeve 47 having sealing means at both ends. Threading 49 is provided which mates with flange 41 and is sealed by seal means 51 shown in FIG. 5a as an o-ring. Swagelok 53 is provided to seal the upper end of the sleeve after insertion of optrode 13 into the bore provided in sleeve 47, flange 41 and window block 35.

In operation optrode 13 is inserted into the block 35 so as to provide light through window 40 and to receive light reflected from the illuminated sample material in block 35. The above described assembly in FIGS. 5 and 5a provide containment of sample material in the event there is any breakage of transparent window 40.

In the practice of this invention it has been found that the introduction of an accurate, representative sample into eductor 6 required cooling the liquid in circulatory pipe 5 below the boiling point of the liquid. Typically, the liquid in circulatory pipe 5 is cooled to a temperature in the range of about 10° C. to 20° C. below the boiling point of the reaction mixture. Further cooling may cause phosphorus to precipitate. If cooling of the material in circulatory pipe 5 is not accomplished, flashing or vaporization of the liquid occurs in the fluid in eductor 6 preventing the eductor from drawing in fresh reactor material at eductor inlet 10. Therefore, in the practice of this invention, the above mentioned cooling of the contents of circulatory pipe 5 is required to provide a representative reactor sample to window 11. Cooling of the contents of circulatory pipe 5 may be accomplished by conventional means such as a heat exchanger or by jacketing an adequate length of the pipe so as to allow cooling fluid to remove a sufficient amount of heat from the system. In FIG. 1 there is shown heat exchanger 21 which is in heat exchange relationship with circulatory pipe 5. During operation the sample in pipe 5 is cooled. Heating may also be accomplished to prevent precipitation of phosphorus when the reactor is shut down.

In operation, the rapid analysis of the contents of the reaction zone of the reactor by means of the laser Raman spectrometer is converted into digital information as input to a computer. The computer is programmed to convert the digitalized analytical information into commands sent to an electrically operated system controlling the amount of phosphorus and/or chlorine fed to the reactor as well as other reactor conditions. Because of the continuous replacement of the sample material in circulatory sample system there is a continuous monitoring of the reaction, in real time, and therefore almost instantaneous control. In practice the laser light through optrode 13 is intermittent such that in a 5 minute period the laser is operated for about 3 minutes. Analysis at regular intervals has proven satisfactory in controlling the reactions.

There has thus been described an automatic system to control the reaction of chlorine and elemental phosphorus in a reactor to produce, in large quantity, phosphorus trichloride. By means of real time analysis of the contents of the reaction zone in the reactor the reaction is run at greater efficiency and the output of the reactor increased over processes employing previously known methods of control of such reactions. The above description employs exemplary physical relationships of the various apparatus employed to carry out the process of the this invention. Because changes may be made in such relationships, to provide different embodiment, the invention is not to be limited by the illustrated examples employed herein to describe the invention. It is intended that the above disclosure shall be interpreted as illustrative and not in a limiting sense.

We claim:

1. An apparatus for the manufacture of phosphorus trichloride comprising a reactor, means for admitting phosphorus trichloride, phosphorus and chlorine into said reactor to create a reaction zone of phosphorus trichloride, dissolved phosphorus and chlorine, a circulating sampling system comprising a pump in association with a circulatory pipe, said circulatory pipe having an eductor inlet in said reaction zone of said reactor, an outlet in said reactor and a transparent window, heat transfer means in communication with said circulating sample system, a laser Raman spectrometer, an optrode and a laser, said optrode comprising a laser light fiber conduit connected to said laser and a plurality of fiber light conduits connected to said spectrometer, a probe head on said optrode connected to said window whereby the contents of the circulatory pipe is irradiated by laser light thereby providing scattered light and at least a portion of the light scattered from said contents is transmitted to said spectrometer through said fiber light conduits for analysis.

2. The apparatus of claim 1 further including means to convert the information produced by said analysis into digital information, a computer means to convert the digital information into electrical signals, an electrical control means for admitting at least one of phosphorus and chlorine into said reactor, whereby the electrical signals control the reactor conditions in the reaction zone.

* * * * *